(12) United States Patent
Panditrao et al.

(10) Patent No.: US 10,450,241 B2
(45) Date of Patent: Oct. 22, 2019

(54) INTEGRATED PROPANE DEHYDROGENATION PROCESS

(71) Applicant: Lummus Technology Inc., Bloomfield, NJ (US)

(72) Inventors: Sunil Shashikant Panditrao, Hackettstown, NJ (US); Sanjeev Ram, Berkeley Heights, NJ (US)

(73) Assignee: Lummus Technology LLC, Bloomfield, NJ (US)

( * ) Notice: Subject to any disclaimer, the term of this patent is extended or adjusted under 35 U.S.C. 154(b) by 0 days.

(21) Appl. No.: 15/706,266

(22) Filed: Sep. 15, 2017

(65) Prior Publication Data

US 2018/0079699 A1 Mar. 22, 2018

Related U.S. Application Data

(60) Provisional application No. 62/395,737, filed on Sep. 16, 2016.

(51) Int. Cl.

| | |
|---|---|
| *C07C 2/66* | (2006.01) |
| *C07C 5/333* | (2006.01) |
| *C07C 5/32* | (2006.01) |
| *B01J 19/24* | (2006.01) |
| *C07C 7/04* | (2006.01) |

(52) U.S. Cl.
CPC .............. *C07C 2/66* (2013.01); *B01J 19/245* (2013.01); *C07C 5/333* (2013.01); *C07C 7/04* (2013.01); *B01J 2219/00103* (2013.01); *B01J 2219/24* (2013.01)

(58) Field of Classification Search
CPC .............. C07C 2/66; C07C 5/333; C07C 5/32
See application file for complete search history.

(56) References Cited

U.S. PATENT DOCUMENTS

| | | | | | |
|---|---|---|---|---|---|
| 5,073,662 | A | * | 12/1991 | Olbrich | .................... B01J 23/60 585/654 |
| 7,842,847 | B2 | * | 11/2010 | Panditrao | .................. C07C 7/04 585/809 |
| 8,013,201 | B2 | | 9/2011 | Panditrao | |

(Continued)

FOREIGN PATENT DOCUMENTS

WO 2015/197733 A1 12/2015

OTHER PUBLICATIONS

International Preliminary Report on Patentability and Written Opinion issued in corresponding International Application No. PCT/US2017/051587 dated Mar. 28, 2019 (11 pages).

*Primary Examiner* — Youngsul Jeong
(74) *Attorney, Agent, or Firm* — Osha Liang LLP

(57) ABSTRACT

Processes and systems for the integrated production of propylene and an alkylate, such as cumene, may include feeding a hydrocarbon feedstock containing propane to a propane dehydrogenation reaction zone to convert a portion of the propane to propylene. The propylene is separated in a separation system to form a polymer-grade propylene stream, a low purity propylene stream, and a propane stream. The low purity propylene stream is then fed to an alkylation reaction zone where the propylene is reacted to produce an alkylated product and generate a low pressure steam. The low pressure steam may then be fed to the separation system as a heat source, integrating the dehydrogenation system and the alkylation system.

12 Claims, 2 Drawing Sheets

(56) References Cited

U.S. PATENT DOCUMENTS

| | | | |
|---|---|---|---|
| 8,242,320 B2* | 8/2012 | Schmidt | C07C 2/66 585/467 |
| 2002/0016520 A1* | 2/2002 | Paggini | C07C 15/085 585/323 |
| 2003/0028059 A1 | 2/2003 | Hamper et al. | |
| 2009/0326307 A1 | 12/2009 | Panditrao et al. | |
| 2010/0310432 A1 | 12/2010 | Schlutz | |
| 2011/0245558 A1 | 10/2011 | Schmidt | |

* cited by examiner

INTEGRATED PROPANE DEHYDROGENATION PROCESS

BACKGROUND

Production of propylene via dehydrogenation of propane conventionally involves a low pressure product splitter that produces a polymer grade propylene (98 wt %+) stream, and little to no propane. These low pressure product splitters require the use of a heat pump to operate, which are costly to run.

Alternatively, as described in U.S. Pat. No. 8,013,201, a high pressure product splitter may be used in the propane dehydrogenation process. In this process, the high pressure column is heated via a closed loop heat exchange cycle, where a heat pump heats and pressurizes a heat exchange medium. The heat exchange medium is pressurized and fed to a heat exchanger where the pressurized heat exchange medium comes into indirect contact with a portion of the product splitter bottoms product. Similar to the use of the low pressure product splitter, the high pressure product splitter requires an external heat source to operate.

Production of cumene is commonly performed by alkylation of benzene with propylene. Conventionally, cumene production also produces a propane gas stream that requires refrigeration and liquefaction to be stored or transported. Low pressure steam may also be made as a by-product of cumene production. The low pressure stream typically cannot be used by the cumene plant's steam system, and in such instances the heat is rejected to air or cooling water.

SUMMARY OF THE CLAIMED EMBODIMENTS

In one aspect, embodiments disclosed herein relate to a process for the production of cumene. First a hydrocarbon feedstock containing propane is fed to a propane dehydrogenation reaction zone to convert a portion of the propane to propylene. The propylene is separated in a separation system to form a polymer-grade propylene stream, a low purity propylene stream, and a propane stream. The low purity propylene stream is then fed to an alkylation reaction zone where the propylene is reacted with benzene to produce an alkylated product and generate a low pressure steam. The low pressure steam may then be fed to the separation system as a heat source.

In another aspect, embodiments disclosed herein relate to a system for the production of cumene. First a propane dehydrogenation reaction zone reacts a hydrocarbon feedstock containing propane to propylene, forming a dehydrogenated effluent and a high pressure steam. A separation system then separates the dehydrogenated effluent into propane, propane/propylene, and a polymer-grade propylene. The propane/propylene may then be reacted in an alkylation reaction zone with benzene to produce an alkylation effluent, and generate a low pressure steam. The alkylation effluent may then be separated in a separation zone to produce two or more fractions including an alkylated product and a propane recycle stream. The propane recycle stream may be at a sufficient pressure to be recycled to the propane dehydrogenation reaction zone without any pressurization or liquefaction.

In another aspect, embodiments disclosed herein relate to a process for the production of propylene and an alkylate of propylene. First a hydrocarbon feedstock containing propane is fed to a propane dehydrogenation reaction zone. In the propane dehydrogenation reaction zone, a portion of the propane is converted to propylene. The propylene product may then be separated, in a separation system, to form a polymer-grade propylene stream, a low purity propylene stream, and a propane stream. The low purity propylene stream may then be fed to an alkylation reaction zone, where propylene is reacted with a hydrocarbon to form an alkylation effluent and generate a low pressure steam. The low pressure steam may then be fed to the separation system to be used as a heat source.

Other aspects and advantages will be apparent from the following description and the appended claims.

DETAILED DESCRIPTION

Figure 1:
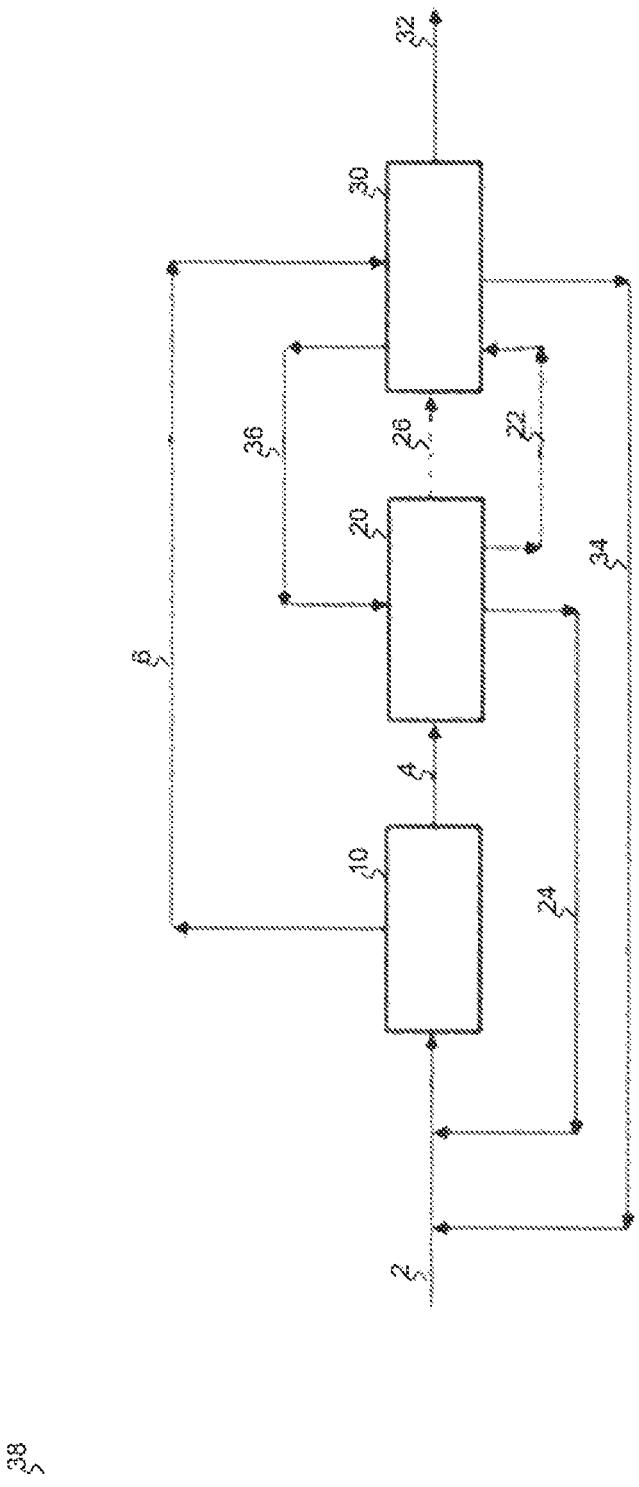
FIG. 1 illustrates a simplified block diagram of a process according to embodiments disclosed herein.

In one aspect, embodiments disclosed herein relate to integrated production of alkylates and olefins, such as propylene. More specifically, embodiments herein relate to integrated processes and systems for producing cumene from a propane feedstock. The process utilizes non-conventional product recycle and heat integration between an alkylation reaction zone and an upstream dehydrogenation reaction zone.

A hydrocarbon feedstock, such as propane, may be fed to a dehydrogenation reaction zone. Within the dehydrogenation zone, the hydrocarbon feedstock may be contacted with a catalyst at appropriate reaction conditions to convert a portion of the propane to propylene. A reaction effluent, including propane and propylene, may then be recovered from the dehydrogenation reaction zone. The reaction effluent may then be separated in a separation system to recover three separate fractions, a low purity propylene stream, a high purity or polymer grade propylene stream, and a stream including unreacted propane. The low purity propylene stream and/or the high purity propylene stream may then be fed to an alkylation reaction zone, where the propylene may be reacted with a hydrocarbon to produce an alkylate product which may be recovered in an alkylation effluent separation zone.

Heat transfer to control reaction temperature during the alkylation reaction may result in production of a low pressure steam stream. Alkylation, when using a low purity propylene feedstock, may produce an offgas including propane. The propane dehydrogenation process may also produce a medium or high pressure steam stream. These and other streams produced as products or byproducts of current processes, such as an offgas from a cumene plant, are generally processed in inefficient manners, resulting in excess operating costs and poor energy usage. Embodiments disclosed herein effectively and efficiently integrate the dehydrogenation reaction zone, dehydrogenation effluent separations, alkylation reaction zone, and alkylation effluent separations, as will be described further below.

In conventional designs for propane dehydrogenation plants, the propane/propylene splitter column is a low pressure splitter that is driven by a heat pump, which is a large power consumer. An alternative to this high energy splitter is to use a high pressure splitter column, which does not require a heat pump but instead uses low quality waste heat. The use of a high pressure splitter reduces or eliminates the power requirements for the heat pump and thereby greatly improves the economics of the propane dehydrogenation plant operation. However, the use of such a high pressure splitter is limited by the amount of low level waste heat available in the propane dehydrogenation plant. For many propane dehydrogenation plant designs, little or no waste heat is available for such a splitter.

In order to overcome the lack of suitable waste heat in the propane dehydrogenation unit, it has been found that the waste heat available from a cumene plant may be effectively and efficiently utilized. Generally the cumene plant will not provide enough waste heat for a splitter capable of handling the entire propane dehydrogenation plant capacity, however. In order to satisfy the heating requirements of the high pressure splitter, a small high pressure splitter may be installed in parallel with a conventional low pressure splitter driven by a heat pump.

Additionally, the energy consumption of the high pressure propane/propylene splitter column in the propane dehydrogenation plant can be significantly reduced by making a low purity propylene product rather than the conventional high purity "polymer grade" product. The low purity propylene product, which is designated "chemical grade" or sometimes "refinery grade", contains a large amount of propane. These low purity grades are not suitable for production of polypropylene, but they may be used for the production of cumene, with suitable adjustments to the cumene plant operating conditions. The propane, which is inert in the cumene plant reactors, may be recovered from the cumene plant, and returned to the propane dehydrogenation plant or to propane storage.

Cumene plants may tolerate lower purity propylene feedstocks. However, typical cumene units using low purity propylene always have refrigeration systems to condense the effluent propane and pump it to high pressure for transport or product storage. In contrast, according to one or more embodiments disclosed herein, it has been found that the propane may be recycled to the dehydrogenation unit without the need for liquefaction or refrigeration.

Accordingly, disclosed herein is a process integrating a propane dehydrogenation unit with an alkylation unit, such as a cumene unit, where the integration allows for the waste heat from the alkylation unit to be utilized to reduce the energy consumption of the propane dehydrogenation unit. The waste heat, in the form low pressure steam, is used to separate a portion of the propylene from unreacted propane in a high pressure splitter column. Power consumption for the heat pump driver of the main propane/propylene splitter column is thereby reduced.

The process also produces two grades of propylene product, a polymer-grade and a chemical-grade. The chemical-grade product may be directly used in the alkylation of benzene to form cumene, for example. In doing so, the transportation or storage cost of propylene may be reduced. Additionally, the unreacted propane in the cumene unit may also be directly recycled to the propane dehydrogenation unit. Typically with cumene units, the propane off-gas needs to undergo pressurization or liquefaction in order to be stored or sold to other facilities. In the integrated processes described herein, the need for such energy intensive processes is negated due to the fact that the propane may be used in a direct recycle.

Additionally, heat generated in the propane dehydrogenation unit may be utilized to reduce the energy consumption in the alkylation unit. High pressure steam generated in the propane dehydrogenation unit may be directly used as a heat source for the alkylation reaction in the cumene unit, thereby reducing the energy cost of the cumene unit even further. As described below, these and other aspects of embodiments herein integrate both energy and product flows.

Referring now to FIG. 1, a simplified process flow diagram of an integrated process according to embodiments herein is illustrated. Although referring generically to a cumene unit in relation to FIGS. 1 and 2, similar benefits may be realized for other alkylation units.

A propane feedstock 2 is fed to a propane dehydrogenation reaction section 10 where a portion of the propane is converted to propylene. During dehydrogenation of propane, a high pressure steam stream 6 is produced. This high pressure steam may be used as a heating medium downstream, such as in the alkylation reaction zone 30, and may be at a pressure in the range of 35 to 45 bar and a temperature in the range of 350° C. to 400° C., for example. The reaction section effluent 4, containing propane and propylene, is fed to a recovery and purification section 20. In the recovery and purification section 20, the propane and propylene are condensed and separated into one or more of a propane/propylene stream 22, a propane recycle stream 24, and a polymer-grade propylene stream 26.

The propane/propylene stream 22, which may contain at least 65 wt % propylene, at least 70 wt %, at least 75 wt %, at least 80 wt %, at least 85 wt %, at least 90 wt %, such as between 80 wt % and 95 wt %, or such as between 85 wt % and 90 wt % propylene, may be fed to an alkylation reaction zone 30. In some embodiments, the propylene stream 22 may be fed to alkylation reaction zone 30 without any intermediate pressurization or processing. The propane recycle stream 24, which may consist essentially of propane, may be recovered from the recovery and purification section 20 and combined with propane feedstock 2 to be used as the feedstock for the propane dehydrogenation reaction section 10. The polymer-grade propylene stream 26, which may have at least 98 wt %, at least 99 wt %, at least 99.5 wt %, or at least 99.8 wt % propylene, may be recovered and sold or alternatively used as feedstock for a downstream process. Alternatively, when needed, such as for column maintenance, polymer-grade propylene 26 may be fed to the alkylation reaction zone 30 for the production of cumene when a propane/propylene stream 22 is not being produced or when additional propylene supply to the cumene unit is required.

In the alkylation reaction zone 30, the propane/propylene stream 22 may be contacted with benzene in the presence of an alkylation catalyst to produce cumene. In the alkylation process, propane is an inert component. After alkylation, the alkylated product is fed to a product separation system. In the product separation system, for example, the alkylation product may be fed to a first separation column where the alkylation product is separated into light gases and a C6+ stream. The first separation column is operated at a top temperature in the range of 100° C. to 160° C., and a pressure in the range of 3 barg to 10 barg. The C6+ stream is fed to a second separation column where benzene is recovered as an overhead product, and components heavier than benzene are recovered as a second bottoms product. The second separation column is operated at a top temperature in the range of 120° C. to 160° C., and a pressure in the range of 2 barg to 7 barg. The benzene stream may be recycled to the alkylation reaction zone. The second bottoms product is fed to a third separation column, operated at a top temperature in the range of 140° C. to 170° C., and a pressure in the range of 0 barg to 2 barg, where cumene product 32 is recovered as an overheads product. Polyalkylate and other heavier components are recovered as a third bottoms product. The light gases are fed to a vent scrubber where propane stream 34 may also be recovered and recycled with propane feedstock 2 as the feedstock for the propane dehydrogenation reaction section 10.

Operating conditions in the product separation system may be maintained such that the propane stream 34 may be at sufficient pressure and quantity to be directly recycled to the dehydrogenation process without the need for any intermediate refrigeration or liquefaction. Typically, in cumene production, the propane stream recovered needs to be either pressurized or liquefied so the propane can be stored, or sold and shipped to another facility. These process are extremely energy intensive and increase with the amount of cumene being produced. The process as disclosed herein lacks these process steps. This lack of refrigeration and liquefaction processes may reduce the overall energy consumption of the alkylation process, making the production of cumene more economical. Alternatively, propane recycle stream 24 may be fed to recovery and purification section 20.

The alkylation reaction zone 30, and the overhead of the second separation column, may result in a low pressure steam 36, which may be used as a heating medium in the recovery and purification section 20. The low pressure steam 36 may be at a pressure of less than or equal to 1 bar, and a temperature in the range of 110° C. to 115° C. Typically, in prior art benzene alkylation processes, the heat generated in the alkylation reaction zone, and from the overhead of the second separation column, is rejected to air or cooling water as there has never been an identified use for such a low quality heating medium.

Figure 2:
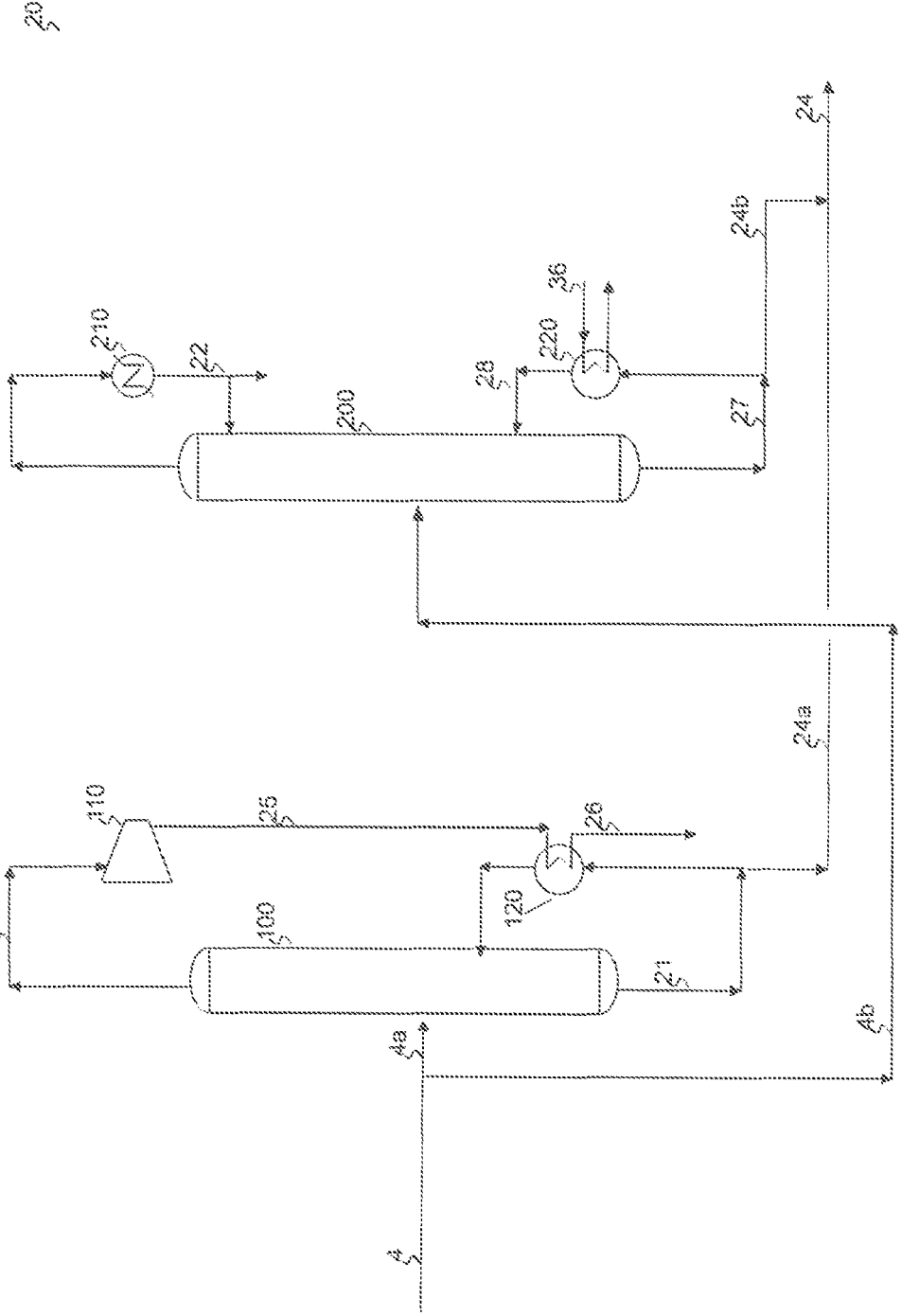
FIG. 2 illustrates an integrated product splitter system useful with embodiments disclosed herein.

Referring now to FIG. 2, a separation system 20 according to embodiments herein is illustrated. Recovery and purification section 20 may include a high pressure splitter in parallel with a low pressure splitter. Like reference numbers represent like parts with reference to FIG. 1.

Recovery and purification section 20 may include two products splitters: a low pressure product splitter 100 and a high pressure product splitter 200, operated in parallel. Reaction section effluent 4, including propane and propylene, may be fed in parallel, via streams 4a and 4b, to splitters 100 and 200, respectively. The feeds may be in the range of 1 to 100% to low pressure product splitter 100 and 1 to 100% to high pressure product splitter 200, such as from 5 to 95%, such as from 20 to 80%, from 35 to 65%, or from 45 to 55%, to splitters 100 and 200 respectively. For example, the ratios of the feed to splitters 100 and 200 may be in the range of 1:1 to 5:1, respectively, or from 2:1 to 4:1, depending on the need for polymer-grade propylene and a propane/propylene mixture. During maintenance, such as on high pressure product splitter 200, the system product can be 100% polymer-grade, a portion of which may be fed to cumene production via flow line 26 (FIG. 1).

A portion of reaction section effluent 4, 4a, may be fed to low pressure product splitter 100. Low pressure product splitter 100 is operated at a pressure in the range of 4 barg to 10 barg, and a temperature in the range of 5° C. to 25° C. The propane and propylene are separated to form a first overhead 23 containing a high purity propylene product, such as a polymer-grade propylene containing 98 wt % or greater propylene. The first overhead 23 is fed to heat pump 110 where it is pressurized to a range of 10 barg to 20 barg. Pressurized propylene 25 is fed to first reboiler 120. Propylene exiting reboiler 120 is collect as high purity propylene product 26. A portion of first bottoms product 21 containing heavies, including propane, is fed through reboiler 120 and heated against the pressurized and heated propylene 25.

The portion of reaction section effluent 4, 4b, not fed to the low pressure product splitter 100, is fed to high pressure product splitter 200. In some embodiments, the high pressure product splitter 200 may be operated at a pressure of between about 12 barg and 26 barg, and at a temperature of about 25° C. to 80° C. A second overhead is collected and water cooled in condenser 210. The condenser effluent is collected as propane/propylene stream 22 and fed to alkylation reaction zone 30 (FIG. 1).

A portion of second bottoms 27 may be fed to second reboiler 220. Second bottoms 27 is heated in second reboiler 220 against low pressure steam 36, which in some embodiments may be low pressure steam from alkylation reaction zone 30 (FIG. 1). Heated bottoms product 28 is fed back to high pressure product splitter 200 to bring the column up to a temperature in the range of 45° C. to 80° C.

A portion of first bottoms product 21 may be recovered via flow line 24a and a portion of second bottoms 27 may be recovered via flow line 24b. These streams may be combined to form propane recycle stream 24. Propane recycle stream 24 may then be recycled and combined with propane feedstock 2 (FIG. 1). In some embodiments propane recycle stream 24 may be at a sufficient pressure and temperature to be recycled directly, without the need for any intermediate pressurization.

As described herein, a small high pressure splitter may be installed in parallel with a conventional low pressure splitter driven by a heat pump. This configuration is generally considered counterintuitive because of the added capital cost associated with parallel splitters. Further, this configuration will produce both polymer-grade propylene as well as chemical-grade propylene, which requires additional capital and operation costs associated with transport of two grades of propylene. However, it has been found that by integrating the systems according to embodiments herein, which may include integration of both product and energy flows, the operating cost savings far outweigh the added capital costs.

Advantageously, it has been found that by using the additional low level heat generated by the alkylation reaction zone, and alternatively the overhead of the second recovery column, in the recovery and purification zone high pressure product splitter, the energy consumption of the propane dehydrogenation reaction zone is correspondingly reduced. A typical cumene production facility will normally just reject this low level heat to the atmosphere as there is no economical means of utilizing it. However, by integrating the cumene production with the propane dehydrogenation process, a viable and economical use for this low level heat has been realized. Additionally, by producing the dilute propylene using the low level heat, less energy is required for the parallel production of polymer-grade propylene.

Additionally, the propane, which is inert in the cumene plant reactors, may be recovered from the cumene plant, and returned to the propane dehydrogenation plant. Because the propane is directly recycled, there is no need for pressurization or liquefaction, which also contributes to a large portion of the energy requirements of a typical cumene plant.

As described above, the process disclosed herein is for a process of producing propylene and a cumene product. However, it is envisioned that the process may be performed with any number of alkylation processes.

For example, according to one or more embodiments disclosed herein is a process for the production of propylene and an alkylate of propylene. In this process, hydrocarbon feedstock, containing propane, may be fed to a propane dehydrogenation reaction zone. In the propane dehydrogenation reaction zone, a portion of the propane may be converted to propylene, producing a dehydrogenation effluent. The dehydrogenation effluent may then be separated to form one or more of a polymer-grade propylene stream, a low purity propylene stream, and a propane stream. The low purity propylene stream may be fed to an alkylation reaction zone, where propylene is reacted with a hydrocarbon to produce an alkylation effluent. In the alkylation reaction zone, low pressure steam stream may also be generated. Such a low pressure steam stream may be used as a heat source in the separation of the dehydrogenation effluent.

The propane stream may be recycled to the propane dehydrogenation reaction zone. The propane stream being recycled may be at a sufficient pressure to be directly recycled without the need for intermediate pressurization or liquefaction.

The alkylation effluent may be separated into one or more of an unreacted hydrocarbon stream, a C3 stream, a alkylate product stream, and a heavies effluent. The C3 stream recovered may be at a higher pressure than the operating pressure of the propane dehydrogenation reaction zone. The higher pressure may allow for the C3 stream, which may contain propane and propylene, to be directly recycled without the need for intermediate pressurization or liquefaction.

Example

In a typical propane dehydrogenation system, a heat pump is required to produce polymer-grade propylene. In a system where 90 MT/h of propane is processed, this heat pump requires, on average, about 33 MW to run. By operating the recovery and purification section with two parallel splitter columns, such that half the feed stream (45 MT/h) goes to each splitter, the columns may be sized smaller, and the overall energy requirement of the propane dehydrogenation process may be reduced. This reduction may be from operating two small parallel columns rather than one large column, reducing the load required by the heat pump.

Typically in cumene production processes, any low level heat generated is vented to the atmosphere, or against cooling water, as the heat duty is considered too poor to be worth using as a heating medium.

In contrast, a system such as that as illustrated in FIGS. 1 and 2, including both a low pressure product splitter and a high pressure product splitter, require less energy. For example, the high pressure product splitter may produce a propane/propylene mixture having 90 wt % propylene, which is suitable for feed to alkylation in the cumene plant. The amount of low pressure steam generated in the cumene plant is approximately 130 MT/h, which may be supplied back to the propane dehydrogenation purification section. This reduces the power requirements of the heat pump to about 25.5 MW, when the low pressure product splitter is in operation, and overall saving of $4.2 mill per year (at $0.07/kWh).

Additionally, high pressure steam generated in the propane dehydrogenation reaction zone may be used to heat the alkylation reactor. A typical cumene alkylation reactor will use approximately 100 MW a year in utility heating. By utilizing the high pressure steam from the propane dehydrogenation reaction zone, the heat duty for the alkylation reactor may be completely satisfied, avoiding the need to import a high temperature heating medium from an outside source.

Further, a typical cumene production facility will use 3 MW in propane pressurization or liquefaction requirements. By recycling propane directly to the propane dehydrogenation zone it may be possible to eliminate the need for pressurization or liquefaction, $2 million per year may be saved.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of cumene comprising:
   feeding a hydrocarbon feedstock comprising propane to a propane dehydrogenation reaction zone, converting a portion of the propane to propylene, forming a dehydrogenated effluent;
   separating the dehydrogenated effluent in a separation system, forming a polymer-grade propylene stream, a low purity propylene stream, and a propane stream;
   feeding the low purity propylene stream to an alkylation reaction zone, wherein propylene is reacted with benzene to concurrently produce an alkylated product comprising cumene and generate a low pressure steam stream; and
   feeding the low pressure steam stream to the separating step as a heat source.

2. The process of claim 1, further comprising recycling the propane stream to the propane dehydrogenation reaction zone.

3. The process of claim 1, further comprising separating the alkylated product into one or more of a benzene stream, a C3 stream, a cumene product stream, and a heavies effluent, wherein the C3 stream comprises one or more of propane and propylene.

4. The process of claim 3, wherein the separating the alkylated product comprises recovering the C3 stream at a higher pressure than an operating pressure of the propane dehydrogenation reaction zone.

5. The process of claim 4, further comprising recycling the C3 stream to the propane dehydrogenation reaction zone as a vapor.

6. The process of claim 5, wherein the recycling is performed without pressurization or liquefaction.

7. The process of claim 1, wherein the low pressure steam stream is at a temperature in a range of 100° C. to 120° C. and a pressure of less than or equal to 1 bar.

8. The process of claim 1, wherein the separation system comprises a low pressure separation column and a high pressure separation column, the process further comprising feeding a first portion of the dehydrogenated effluent to the low pressure separation column and feeding a second portion of the dehydrogenated effluent to the high pressure separation column.

9. The process of claim 8, wherein a feed ratio of the first portion of the dehydrogenated effluent and the second portion of the dehydrogenated effluent is in a range of 1:1 to 5:1.

10. The process of claim 8, further comprising operating the low pressure separation column at a temperature in a range of 5° C. to 25° C. and a pressure in a range of 4 barg to 10 barg and operating the high pressure separation column at a temperature in a range of 25° C. to 80° C. and a pressure in a range of 12 barg to 26 barg.

11. The process of claim 8, further comprising producing a propylene product comprising at least 98 wt % propylene from the low pressure separation column, and producing a propylene product comprising 60-95 wt % propylene from the high pressure separation column.

12. The process of claim 1, further comprising:
concurrently generating a high pressure steam stream in the propane dehydrogenation reaction zone; and
feeding the high pressure steam stream to the alkylation reaction zone as a heat source.

\* \* \* \* \*